(12) United States Patent
Colvin, Jr. et al.

(10) Patent No.: US 7,713,745 B2
(45) Date of Patent: May 11, 2010

(54) NON-COVALENT IMMOBILIZATION OF INDICATOR MOLECULES

(75) Inventors: Arthur E. Colvin, Jr., Mt. Airy, MD (US); Carrie R. Lorenz, Woodbine, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 1109 days.

(21) Appl. No.: 10/822,670

(22) Filed: Apr. 13, 2004

(65) Prior Publication Data

US 2005/0227242 A1 Oct. 13, 2005

(51) Int. Cl.
*G01N 21/63* (2006.01)
*G01N 21/64* (2006.01)

(52) U.S. Cl. .................. 436/172; 436/85; 506/43
(58) Field of Classification Search .............. None
See application file for complete search history.

(56) References Cited

U.S. PATENT DOCUMENTS

| | | | |
|---|---|---|---|
| 5,356,417 A | 10/1994 | Golds | |
| 5,503,770 A | 4/1996 | James | |
| 5,517,313 A | 5/1996 | Colvin, Jr. | |
| 5,894,351 A | 4/1999 | Colvin, Jr. | |
| 5,910,661 A | 6/1999 | Colvin, Jr. | |
| 6,001,936 A | 12/1999 | Barrera et al. | |
| 6,011,984 A | 1/2000 | Van Antwerp | |
| 6,304,766 B1 | 10/2001 | Colvin, Jr. | |
| 6,330,464 B1 | 12/2001 | Colvin, Jr. | |
| 6,344,360 B1 | 2/2002 | Colvin, Jr. | |
| 6,400,974 B1 | 6/2002 | Lesho | |
| 2002/0026108 A1 | 2/2002 | Colvin, Jr. | |
| 2002/0039793 A1 | 4/2002 | Colvin, Jr. | |
| 2002/0055007 A1 | 5/2002 | Soane et al. | |
| 2002/0090734 A1* | 7/2002 | Daniloff et al. ............... 436/95 |
| 2002/0106810 A1* | 8/2002 | Singaram et al. ............ 436/172 |
| 2002/0127626 A1 | 9/2002 | Daniloff | |
| 2003/0003592 A1 | 1/2003 | Colvin, Jr. | |
| 2003/0008408 A1 | 1/2003 | Colvin, Jr. | |
| 2003/0013202 A1 | 1/2003 | Colvin, Jr. | |
| 2003/0013204 A1 | 1/2003 | Colvin, Jr. | |
| 2003/0082663 A1 | 5/2003 | Daniloff | |
| 2004/0006387 A1* | 1/2004 | Kelman ..................... 623/6.36 |

FOREIGN PATENT DOCUMENTS

EP 0492126 A2 7/1992

OTHER PUBLICATIONS

Kwok et al 2004 Polymer 45:4017-4027.*
International Search Report from corresponding International Application PCT/US2005/011654, Jul. 26, 2005.

* cited by examiner

*Primary Examiner*—Christopher Low
*Assistant Examiner*—Christopher M Gross
(74) *Attorney, Agent, or Firm*—Rothwell, Figg, Ernst & Manbeck PC

(57) ABSTRACT

The invention relates to immobilization methods, in particular for immobilizing indicator molecules on supports such as sensors and to sensors having those molecules immobilized to their surface. Non-covalent immobilization of macromolecular indicator molecules on those supports via mechanical interlacing with polymers at the surface of a support and via ionic bonding via charged moieties of indicator molecules and ionic groups on the surface of the support are disclosed.

31 Claims, 8 Drawing Sheets

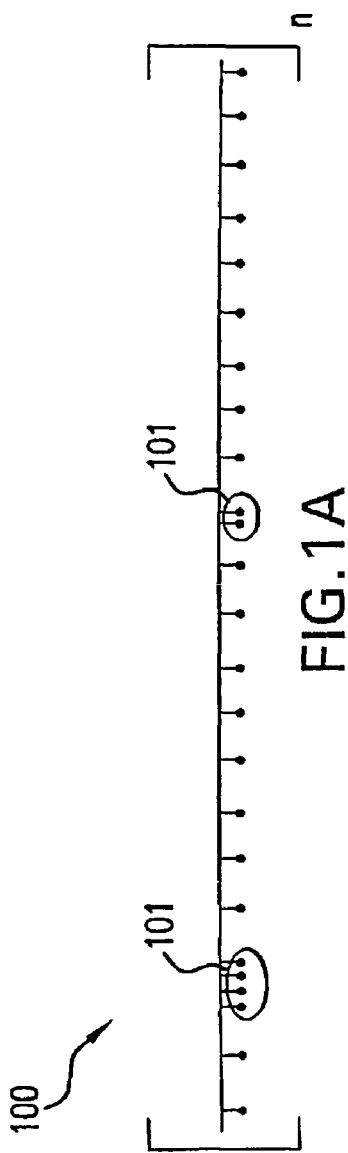
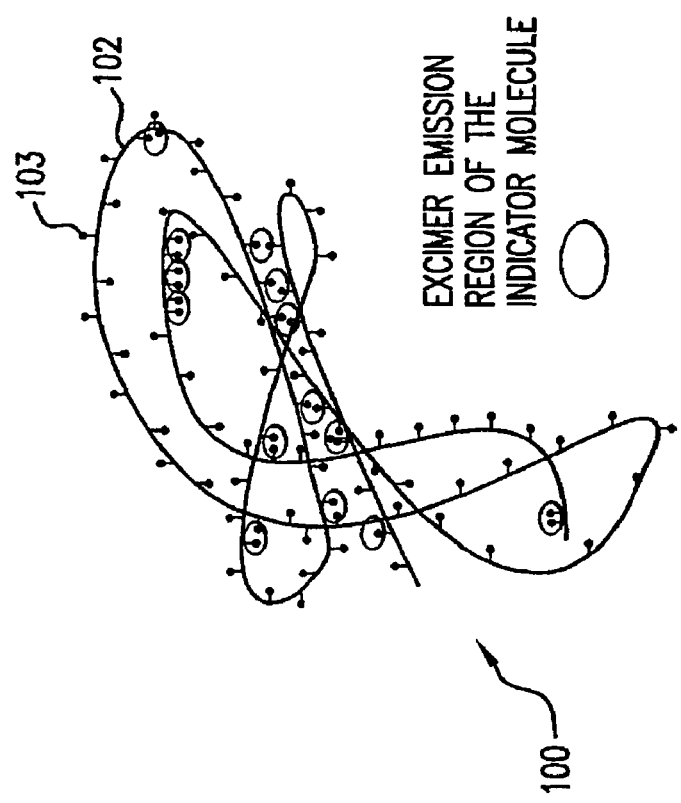

MOLECULAR LEVEL "MANY" X MAGNIFICATION

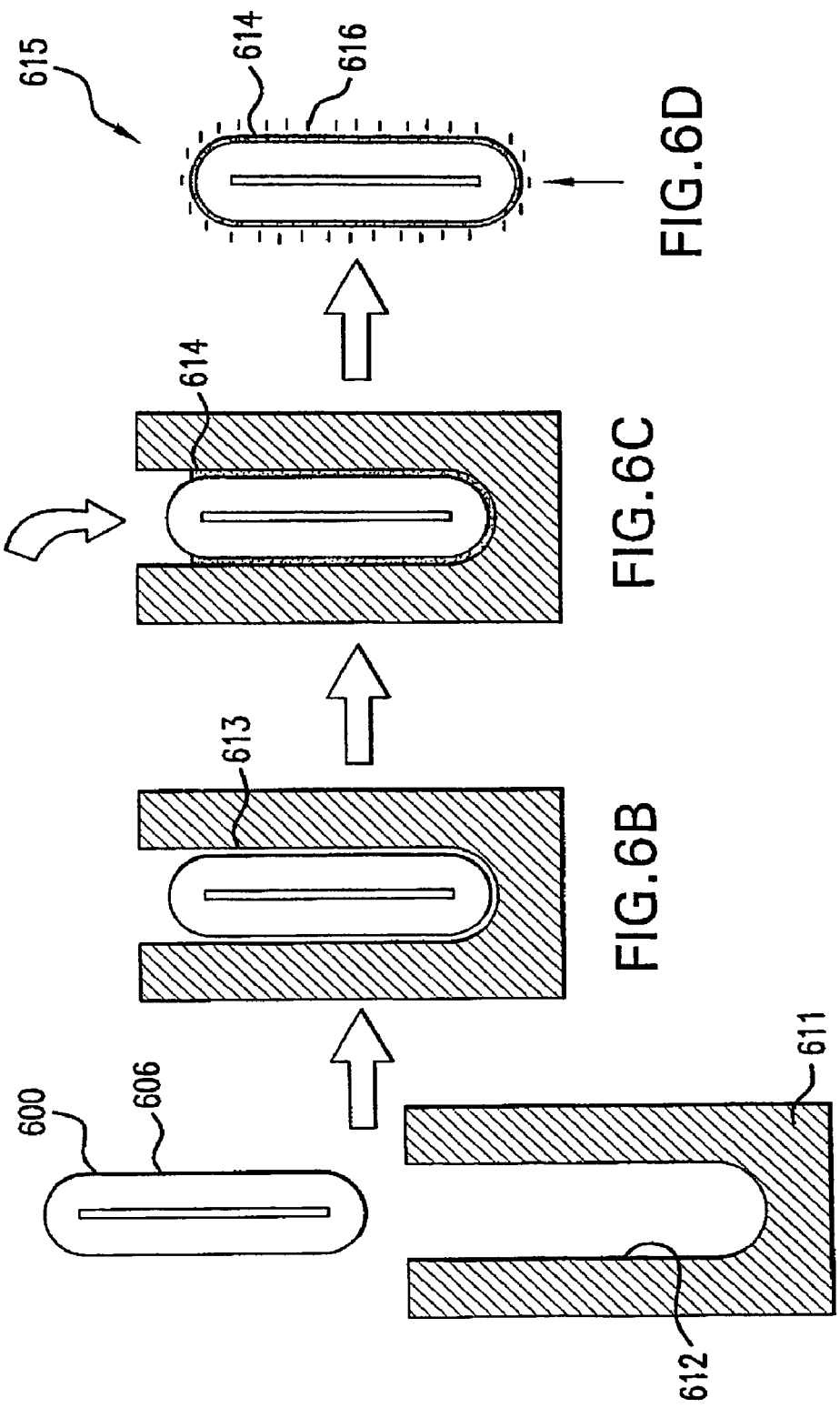

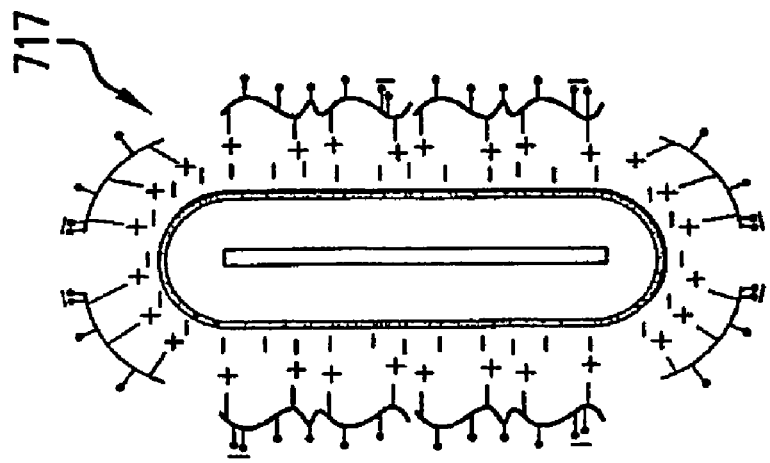
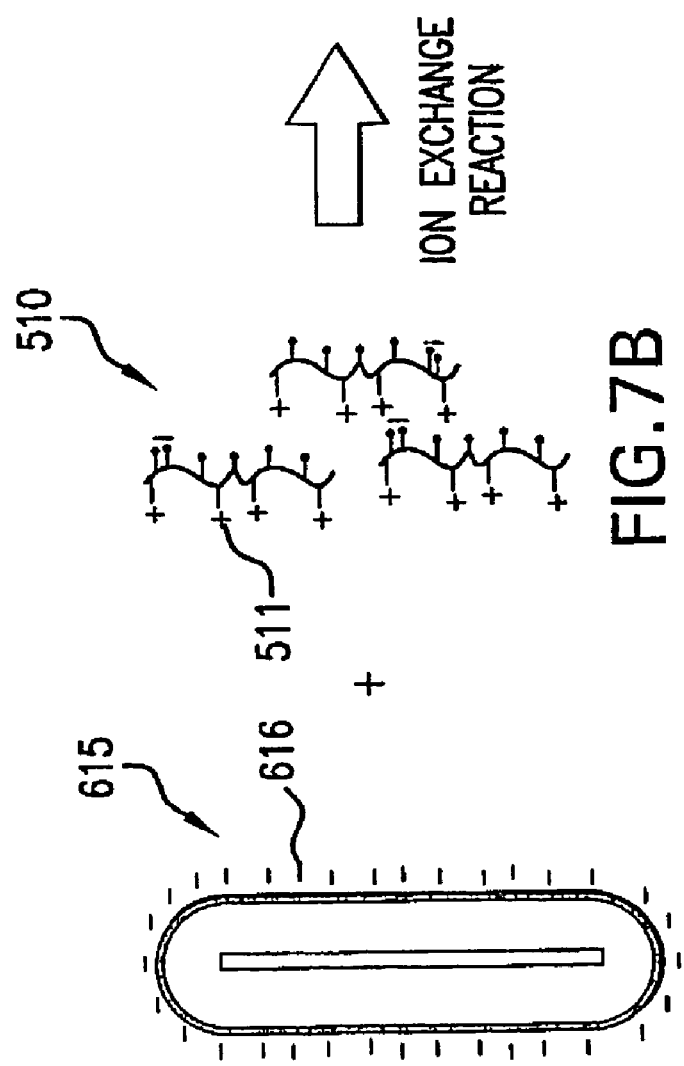

ION EXCHANGE REACTION

NON-COVALENT IMMOBILIZATION OF INDICATOR MOLECULES

BACKGROUND OF THE INVENTION

1. Field of the Invention

The invention relates to immobilization methods and, in particular, for immobilizing indicator molecules on supports such as optical sensors, and to sensors having those indicator molecules immobilized on their surfaces.

2. Description of the Related Art

U.S. Pat. No. 5,356,417 describes a fluorescent-based sensing device comprising indicator molecules and a photosensitive element, e.g., a photodetector. Broadly speaking, in the context of the field of the invention, indicator molecules are molecules where one or more optical characteristics of which is or are affected by the local presence of an analyte. Indicator molecules have been used to measure a wide array of analytes, such as glucose, oxygen, toxins, pharmaceuticals or other drugs, hormones, and other metabolic analytes. These indicator molecules are often classified based on the chemical principal on which their activity is based. For example, the activity of many indicators, such as the one described in U.S. Pat. No. 6,344,360, the disclosure of which is incorporated herein by reference, are based on the principle of luminescence, in particular fluorescence. U.S. Pat. No. 6,344,360 describes a fluorescent indicator molecule containing a fluorescent lanthanide metal chelate complex whose fluorescence emission intensity is increased by the presence of certain sugars. Other categories of indicator molecules include calorimetric indicator molecules which change their color in the presence of an analyte and indicator molecules which change absorbency at a particular wavelength.

Indicator molecules vary widely in their chemical compositions and properties. For example, indicator molecules may be monomeric or polymeric and/or hydrophilic or hydrophobic.

Indicator molecules have been immobilized on supports, such as sensor surfaces, by attaching the indicator molecule at the surface of the support. Immobilizing indicator molecules on inert polymeric substrates poses a particular challenge, since those substrates have to be modified to create or chosen to provide attachment points for the indicator molecules.

Molecules can be immobilized on a substrate in different ways. Immobilization is often based on covalent links between the substrate and the immobilized molecule. To facilitate immobilization, inert substrates are generally avoided, as those require pretreatments, e.g., with U.V. or with harsh acids such as nitric acid to achieve oxidation of the substrate to create reactive sites. These pretreatments are generally associated with undesirables, such as instability of the immobilization product or the handling of harsh acids. Thus, more readily modifiable supports, such as polyacrylamide supports, are generally chosen to attach molecules of interest. A polyacrylamide support can, for example, be readily modified, for example, by attaching through reactive amine groups, which enables attachment of a wide variety of molecules, including haptenes, peptides, carbohydrates and oligonucleotides.

The immobilization of molecules, such as indicator molecules, on optical sensors poses some unique challenges. For example, it is important that the immobilization method does not interfere with the function of the optical sensor. Also, certain immobilization methods might result in the discoloration of a support and thus, interfere with its function as optical waveguide. Known immobilization methods can also change the optical properties of the surface by, e.g., causing bubbling or rippling of the surface, thus disrupting the optical path of a sensor or adversely affect material properties. Thus, there is a continuing need for improvements in the way indicator molecules are immobilized on an immobilization substrate. This need is particularly conspicuous in the context of immobilizing indicator molecules on sensor bodies, in particular on optical sensor bodies, used as long term implants.

SUMMARY OF THE INVENTION

In a first aspect, the present invention is directed to a method for non-covalently attaching a macromolecular indicator molecule to a support. This method comprises (a) providing a support surface comprising at least one polymer, (b) changing the integrity of the polymer to provide loosened polymer chains that form at least one interlacing area, (c) providing at least one macromolecular indicator or monomers thereof, (d) causing the macromolecular indicator or polymerization products of monomers thereof to interlace with the interlacing areas, and (e) causing the loosened polymer chains to tighten to produce surface immobilized indicator molecules. In this first aspect of the present invention, the macromolecular indicator molecule in (c) may be a partially or fully polymerized indicator molecule. Alternatively, the monomers of the at least one macromolecular indicator molecules in (c) may be sequentially polymerized in (d) to form a sequential IPN (interpenetrating polymer network).

The polymer chains may be loosened by a solvent such as, for example, ethanol, 2-methoxyethanol, dimethylformamide, a monomer of a hydrophilic macromolecular indicator such as HEMA or mixtures thereof. The polymer chains may be tightened again by the removal of the solvent or by polymerization of the monomer into the hydrophilic macromolecular indicator, respectively. In this aspect of the invention, the support surface may be hydrophobic and the macromolecular indicator molecule may be hydrophilic. The support may be the surface of a sensor or an optical waveguide. The macromolecular indicator molecule may have one or more reference regions. These reference regions may be excimer regions or may comprise or consist of at least one reference molecule. The macromolecular indicator molecule may also comprise one or more crosslinkers, which in turn crosslink the macromolecular indicator molecule within the support.

In a second aspect, the present invention is directed to a graft. The graft preferably comprises a surface including at least one polymer and a macromolecular indicator molecule. The graft is characterized in that the macromolecular indicator molecule is stably interlaced between at least one chain of at least one of the polymers of the support. In accordance with one embodiment of the invention, the macromolecular indicator molecule in the graft has certain properties that substantially correspond to the properties of an identical macromolecular indicator molecule that is not part of a graft (native molecule). Those properties may include, but are not limited to, the molecule's affinity to an analyte or its reference regions, such as excimer regions, which, in the native molecule, may be a result of the molecule's primary and/or tertiary structure. The surface of the graft may be a sensor.

In a third aspect, the present invention is directed to another method for non-covalently attaching an indicator molecule to a sensor. The method comprises (a) providing a support having a surface comprising at least one strong ionic group, (b) adding to the surface at least one indicator molecule comprising at least one charged residue having a charge opposite of that of the ionic group, (c) immobilizing the indicator molecule on the support via an ionic bond between the ionic group of the support and the at least one charged residue. The ionic group, for example, may be an anionic group, in particular, a sulfonate. The at least one charged residue, for example, may be a positively charged residue. The ionic group may be part of a copolymer of, for example, sulfonate and methyl methacrylate, which forms a coat on the surface of the support.

In a fourth aspect, the present invention is directed to a sensor for determining the presence or concentration of an analyte within a medium. The sensor comprises a sensor body preferably having a polymeric outer surface surrounding the sensor body, and a macromolecular indicator molecule which, in response to the presence of an analyte in the medium, changes at least one measurable characteristic. The sensor further comprises a detector which detects radiation from the indicator molecules and which generates an electrical signal which corresponds to the changes in at least one characteristic of the indicator molecule which is indicative of the presence or concentration of the analyte. In this sensor, the macromolecular indicator molecule may be stably interlaced between at least one chain of at least one of the polymer chains of the sensor surface. The sensor may be an optical sensor which is adapted to detect one or more analytes of interest in a medium, such as glucose. In a preferred embodiment, the surface of the sensor may be made from polymethylmethacrylate.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person skilled in the art to make and use the invention. In the drawings, like reference numbers indicate identical or functionally similar elements. Additionally, the left most digit(s) of a reference number identifies the drawing in which the reference number first appears.

FIGS. 1A and 1B is a schematic illustration of the primary and tertiary structure of a water soluble macromolecular indicator molecule according to the present invention.

FIGS. 6A to 6C show a mechanism for coating a support with a copolymer containing ionic groups in accordance with one aspect of the present invention.

FIG. 6D shows the final product of the mechanism shown in FIGS. 6A to 6C.

FIGS. 7A to 7C show how a macromolecular indicator molecule carrying positive charges which are distributed over the entire molecule is attached to the body of a sensor having anionic groups on its surface.

DETAILED DESCRIPTION OF THE INVENTION

Figure 2B:
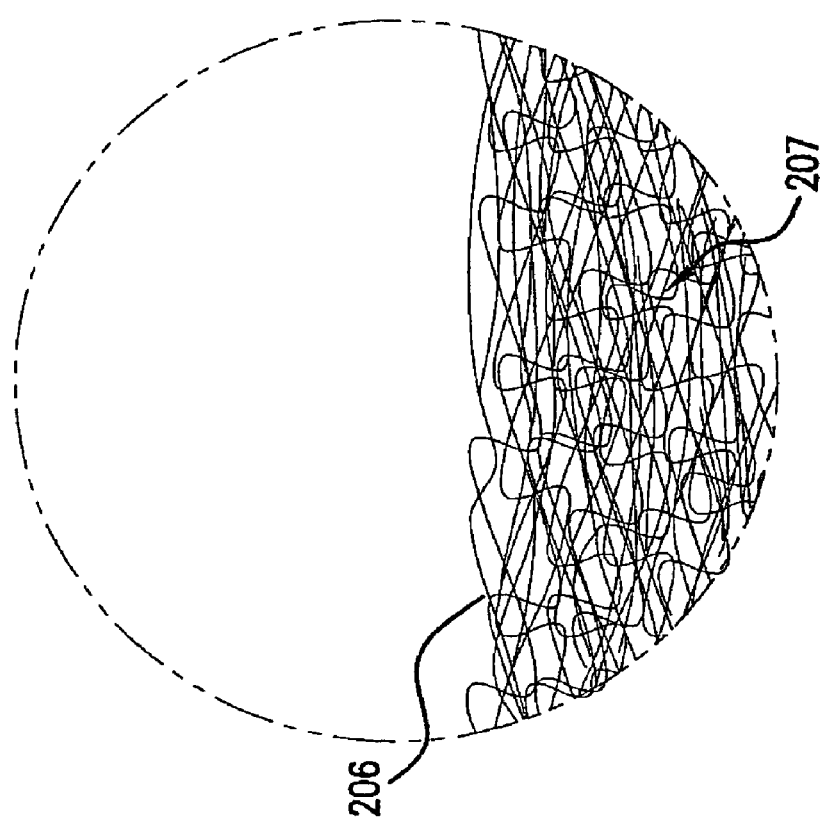
FIGS. 2A and 2B show an immobilization support for immobilizing indicator molecules in accordance with one embodiment of the present invention.

The support for an indicator molecule, such as a sensor device, has to meet certain design requirements. In the case of an optical sensor housing, translucency and durability are generally desirable. As a result, the surface of a support, which may be made of a material that can act as an optical waveguide, often has a set of properties that is very different from the properties of the indicator molecule that is desired to be attached to that surface. This set of properties is also often different from the environment in which the sensor operates. For example, the support is often very hydrophobic (e.g. for the protection of the microelectronics within the sensor) while an indicator molecule can be very hydrophilic. This is especially desirable if analytes are detected in an aqueous medium. Certain embodiments of the present invention are directed at achieving effective immobilization of indicator molecules, including macromolecular indicator molecules, despite the differences in the properties of the support and the indicator molecule, and without adversely affecting the performance of the indicator molecule. Certain embodiments of the present invention actually take advantage of these differences, enhance them and/or even create them to achieve immobilization.

A wide variety of indicator molecules can be used in the context of the present invention. An indicator molecule according to the present invention is a molecule having at least one characteristic, such as fluorescence, that is affected by the local presence of an analyte. Such an indicator molecule can base its activity on any number of principles including, but not limited to, luminescence, such as fluorescence and phosphorescence, absorbance or colorimetrics. The indicator molecules of the present invention include monomeric molecules as well as macromolecular indicator molecules, such as water soluble macromolecular indicator molecules. For example, the compounds described in U.S. patent application Ser. No. 10/187,903 {now U.S. Pat. No. 6,800,451} and in U.S. patent Publication Nos. 2002/0127626 or 2003/0082663, which have at least two recognition elements for glucose, can be used in the context of the invention. Further, the fluorescent lanthanide metal complexes described in U.S. Pat. No. 6,344,360 or the fluorescent phenylboronic compounds of U.S. Pat. No. 5,503,770 also can be used in the context of the present invention. The disclosures of these patents and applications are incorporated herein by reference. However, as the person skilled in the art will appreciate, any other suitable indicator molecule can be used as well.

The indicator molecules of the present invention are generally specific for one or more analytes. For example, in a preferred embodiment, the indicator molecules are specific for glucose. In other embodiments, the indicator molecules are specific for oxygen, carbon dioxide, nitric oxide, toxins, pH, ions and mono- or divalent cations. However, as the person skilled in the art will appreciate, a wide variety of other analytes can be detected and/or measured using the present invention.

In certain embodiments of the present invention, monomeric molecules such as those described in the above-mentioned patents and applications, are converted into macromolecular indicator molecules, including water soluble macromolecular indicator molecules, by polymerization in the presence of expanded substrate polymer, or attachment to a polymer. "Macromolecular indicator molecules" or "macromolecular indicators" according to the present invention are molecules acting as indicator molecules, and are macromolecular from, for example, being partially or fully polymerized, for example, copolymerized, with one or more molecules of another type. A polymer, in the context of the present invention, includes any product of the polymerization of monomers, complex or simple ones, as well as oligomers. "Water soluble macromolecular indicator molecules" (WSMIM) according to the present invention are macromolecular indicator molecules which are overall substantially hydrophilic. In order to obtain a WSMIM, suitable recognition monomers can be co-polymerized with hydrophilic monomers. Examples of suitable hydrophilic monomers include, but are not limited to, methacrylamides, certain methacrylates, vinyls, polysaccharides, polyamides, polyamino acids, hydrophilic silanes or siloxanes, HEMA (hydroxyethyl methacrylate) or other common hydrogel constituents as well as mixtures of two or more different monomers. Examples of macromolecular indicator molecules produced by co-polymerization of a monomeric indicator molecule with a hydrophilic monomer are described in U.S. patent Publications Nos. 2003/0013204, 2003/0013202, 2003/0008408, 2003/0003592, 2002/0039793 and in U.S. patent application Ser. No. 10/187,903, incorporated herein by reference.

The nature and ratio of suitable hydrophilic monomers will vary according to a number of factors described, for example, in patent Publication No. 2003/0013204. In a preferred embodiment, the water soluble macromolecular indicator molecule is a copolymer of 2-hydroxy methacrylate (HEMA) and bis-carboxylate bis-boronate-anthracene. In yet another preferred embodiment, the water soluble macromolecular indicator molecule is a copolymer of methacrylamidopropyltrimethylammonium chloride (MAPTAC) and bis-carboxylate bis-boronate-anthracene at ratios between approximately 5:1 to 80:1.

In a preferred embodiment, the macromolecular indicator molecules of the present invention have reference regions such as excimer regions, which are also referred to as excimer emission regions. "Excimer regions" according to the present invention refers to the region of a macromolecular indicator molecule that provides an excimer effect. Sequence specific excimer regions exist as a direct result of the primary structure of a molecule. However, adoption of its tertiary structure (3-D configuration) may create additional excimer regions in a molecule. "An excimer effect" in the context of the present invention refers to a characteristic longer wavelength emission of a molecule having excimer regions. The molecular basis of an excimer effect is described, for example, in U.S. Publication No. 2003/0013204, incorporated herein by reference.

As described therein, an excimer region is not responsive to changes in analyte concentration, but is responsive to other aspects of the system analyzed, such as excitation intensity, temperature, and pH. As a result, an indicator molecule having excimer regions may serve as both an indicator and an internal reference. For example, the emission intensity at the indicator wavelength (i.e., the wavelength influenced by the analyte) can, via select bandpass filters, be separated optically from the emission intensity at the excimer wavelength. The resultant value corrects for interfering factors which affect fluorescent emission properties, such as fluorescent quenching by, for example, oxygen, drift, photobleaching, degradation and error in pH etc. Indicator molecules having excimer regions are particularly useful for applications involving long-term implantation, as ambient conditions in any long-term in vivo application are bound to be subject to frequent change. Accordingly, molecules with excimer regions are part of a preferred embodiment of the present invention. U.S. patent Publications Nos. 2003/0013204, 2003/0013202, 2003/0008408, 2003/0003592 and 2002/0039793, incorporated herein by reference, describe examples of such molecules.

In another embodiment of the present invention, the macromolecular indicator molecules comprise one or more reference molecules. Reference molecules are, for example, fluorescent molecules that emit at wavelengths different from the respective indicator molecule and are not responsive to changes in analyte concentration, but responsive to other aspects of the system analyzed, such as excitation intensity, temperature, and pH.

FIGS. 1A and 1B show the primary structure and tertiary structure of a representative WSMIM 100 according to the present invention, respectively. The tertiary structure of such a molecule is generally governed by the lowest energy configuration which it may attain in an aqueous environment. The molecule has, in the embodiment shown, excimer emission regions 101, some of which are created by the folding of the molecule 102. In those excimer emission regions, two planar molecules of aromatic structure (e.g. fluorophores) are oriented in coplanar configuration and have overlapping pi-electron orbitals. This results in one or more emissions at a wavelength that is different from the wavelength characteristic for the parent species 103. For example, for fluorescent planar species, a characteristic downfield emission occurs in comparison to that of the uncoupled species at a wavelength of substantially lower energy than the uncoupled species. As described above, this characteristic emission can be used to compensate for variable ambient conditions.

In certain embodiments of the present invention, indicator molecules having at least one strong positively or negatively charged moiety at a suitable pH are preferred. The pH that allows a moiety to carry a strong negative or positive charge depends directly on the nature of the moiety. In a preferred embodiment, the moiety may be chosen according to the environment in which the indicator molecule is used. Accordingly, a "suitable pH", in a preferred embodiment, may be the prevailing pH in the environment of choice. Thus, in a preferred embodiment, for in vivo applications of sensors that are submerged in prevailingly neutral bodily fluids, indicator molecules that are strongly ionic at neutral pH are preferred. For example, at pH values near neutral, amine moieties are strongly positively charged and can form a strong ionic bond with a sulfonate that is strongly negatively charged at this pH.

The indicator molecules may be indicator molecules that inherently contain strongly positively or negatively charged moieties at a suitable pH or indicator molecules that have been modified to include such moieties by, for example, attaching them to a molecule that contains one or more strong positively or negatively charged moieties, such as MAPTAC or 2-Acryloxyethyltrimethylammonium chloride.

Figure 5A:
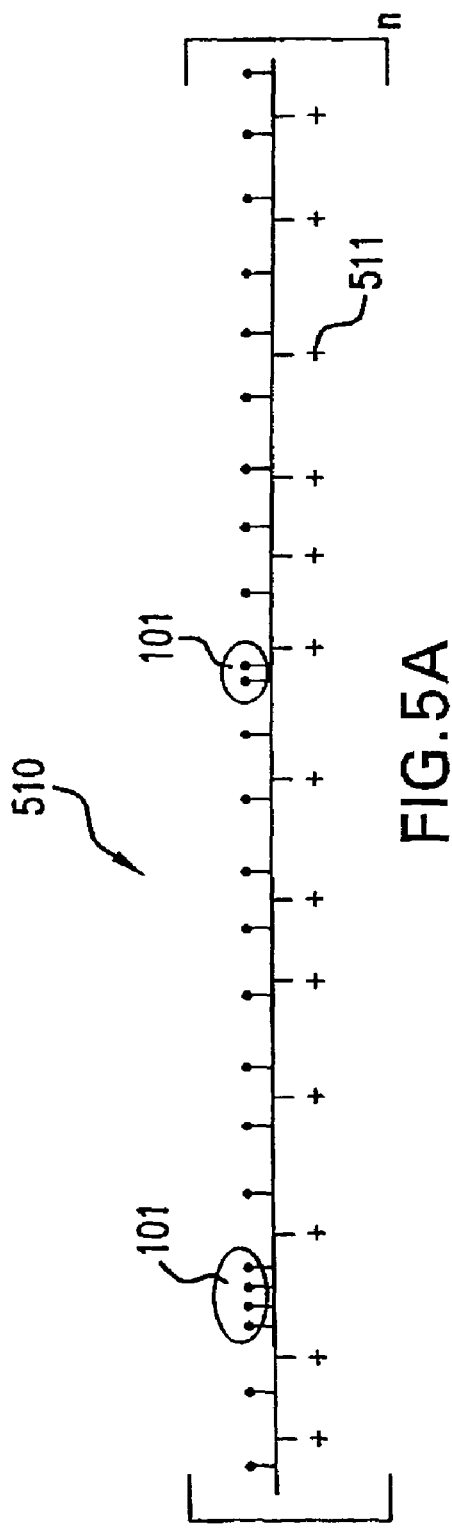
FIGS. 5A and 5B show macromolecular indicator molecules containing one or more positively charged moieties and excimer regions.
Figure 5B:
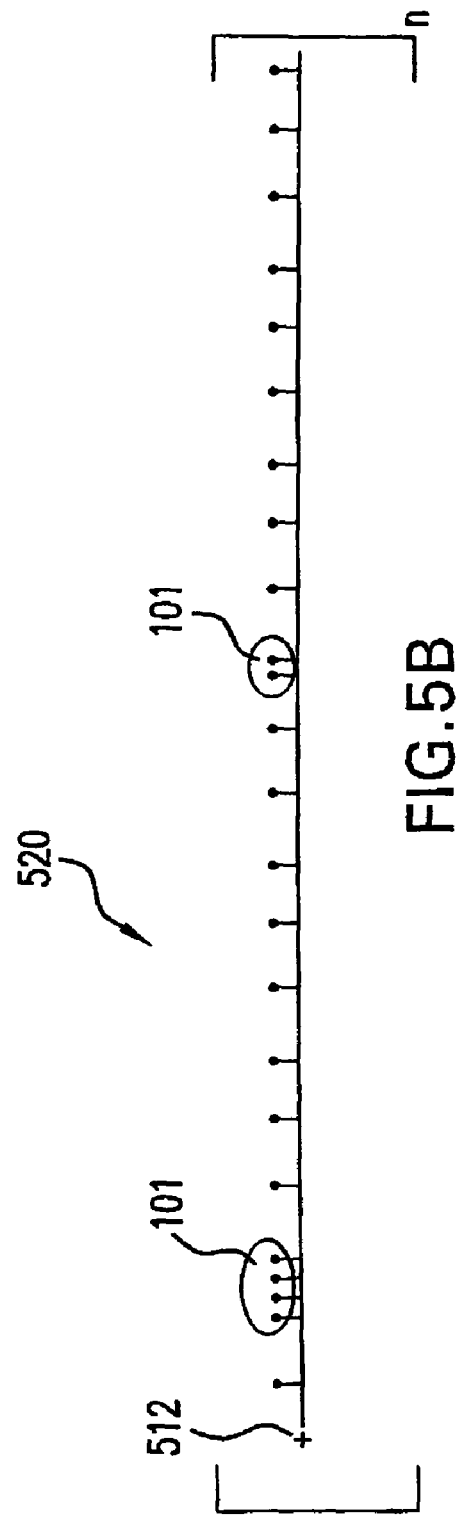

FIGS. 5A and 5B show representative cationic macromolecular indicator molecules containing one or more strong positively charged moieties. In particular, FIG. 5A illustrates a cationic macromolecular indicator molecule 510 containing a plurality of strong positively charged moieties 511. FIG. 5B illustrates a cationic macromolecular indicator molecule 520 having one strong positively charged moiety 522. The molecule of FIG. 5A is positively charged as a result of a large number of positively charged moieties, such as amine moieties, which are distributed over the entire molecule 510. In contrast, the molecule 520 of FIG. 5B contains only a terminal positive charge 522, for example, in the form of an amine moiety. As indicated by the letter "n" in both figures, the molecules can be substantially longer than depicted in these figures. The illustrated indicator molecules also have excimer emission regions 101 that are present in the primary structure of the molecule. The advantages of using indicator molecules having such regions has been described above.

In a preferred embodiment, the support on which an indicator molecule is immobilized (hereinafter "immobilization support") is a sensor. Examples of suitable sensors are described in U.S. Pat. Nos. 5,517,313; 5,910,661; 5,894,351, whose disclosures are incorporated herein by reference. Examples of suitable implantable sensors are disclosed in U.S. Pat. Nos. 6,330,464; 6,011,984; 6,304,766; 6,400,974 and patent application Publication No. 2002/0026108, the disclosures of which are incorporated herein by reference. However, as the person skilled in the art can appreciate, other sensors may be used.

In a preferred embodiment, an immobilization support may be formed from an optically transmissive polymer material. Preferred polymer materials include, but are not limited to, acrylic polymers such as polymethylmethacrylate (PMMA), polyhydroxypropylmethacrylate, polystyrene, and polycarbonates such as those sold under the trademark LEXAN. The most preferred material is PMMA.

Sensors and supports having indicator molecules attached to them according to the present invention can be used in a wide variety of fields. For example, they can be used to detect sub-levels or supra-levels of glucose in physiological buffers or fluids, such as blood, plasma, serum, interstitial fluid, cerebrospinal fluid, urine, saliva, intraocular fluid, lymph, tears, or sweat, thus providing valuable information for diagnosing or monitoring such diseases as diabetes and adrenal insufficiency. Other uses have been described elsewhere, for example, in U.S. patent application No. 2003/0082663. However, the sensors and supports having indicator molecules attached to them according to the present invention are particularly useful for long term in vivo uses, such as long term implants.

Figure 2A:
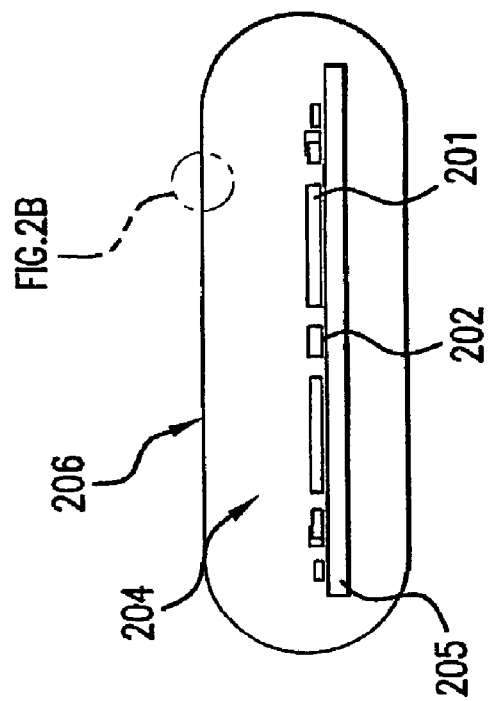

FIGS. 2A and 2B illustrate a representative immobilization support that may be used in the context of the present invention. In particular, FIGS. 2A and 2B show a polymer encasement 204 containing microelectronics 205 of a representative electro-optical sensing device. The microelectronics 205 may comprise microelectronic components such as, for example, a radiation source 202 and a detector 201. In one preferred embodiment, radiation source 202 is an LED, although other radiation sources may be used. Also in one preferred embodiment, detector 201 is a photosensitive element (e.g. a photodetector), although other detecting devices may be used. Microelectronics that may be contained in a representative electro-optical sensing device are described in U.S. Pat. No. 6,330,464, the disclosure of which is incorporated herein by reference.

As shown in more detail in FIG. 2B, the surface 206 of the immobilization support comprises a polymeric structure 207, such as, for example, the chains of PMMA, which are interwoven and intertwined. This polymeric structure provides, in one embodiment of the present invention, a hard, solid, hydrophobic boundary to its surrounding and is inert to reaction.

In certain aspects of the present invention, a macromolecular indicator molecule is interlaced with the support without substantially affecting its properties, in particular its affinity to an analyte and/or its reference regions, such as excimer regions, which in the native molecule, are a result of the molecule's primary or tertiary structure. Maintaining the properties of the indicator molecule will ensure that the detection ability of the indicator molecule is not negatively affected. In another preferred embodiment, the macromolecular indicator molecule is attached to the support in a way that makes its analyte binding regions highly accessible.

In one preferred embodiment, the character of the bulk support material is also substantially preserved after immobilization. This will ensure that a primary function of the support, for example, the encasement of microelectronics, is not negatively affected by the immobilization. In a preferred embodiment, this goal is achieved by relying on non-covalent mechanical interlacing for immobilization.

In another preferred embodiment, the indicator molecule is associated with the support in a way that the diffusion distance of an analyte may be maintained relatively low. For example, the diffusion distance of an analyte is maintained at approximately 200 microns or less, preferably 150 microns or less, more preferably 125 microns or less, or the diffusion distances of an analyte may also be maintained at approximately 80 microns or less, more preferably less than approximately 50 microns and, in certain instances, as low as approximately 1 micron. Maintaining the diffusion distance relatively low will maintain the response time of the sensor to which the indicator molecule is attached relatively low. For example, response times may be, for example, less than about 8 minutes, preferably less than about 6 minutes, more preferably less than about 5 minutes. In one non-limiting embodiment, for the detection of glucose in an aqueous medium, a diffusion distance of approximately 100 microns or less and a response time of approximately 5 minutes or less may be desirable. In another non-limiting embodiment, for the detection of oxygen gas, a diffusion distance of approximately 50 microns and a response time of approximately 50 milliseconds may be desirable. Maintaining the response time of the indicator molecule relatively low will allow, for example, in the case of a sensor, close to real time monitoring of the concentration and/or presence of a given analyte.

In one aspect of the present invention, the macromolecular indicator molecule that is to be immobilized on a support may be hydrophilic. In a preferred embodiment of this aspect of the invention, the hydrophilicity of the macromolecular indicator molecule is substantially maintained after immobilization to the support. In another preferred embodiment, the macromolecular indicator is associated with the support in a way that maintains the micro environment of the macromolecular indicator sufficiently hydrophilic, preferably hydrophilic enough to allow free and saturating diffusional access to large portions of the entire macromolecular indicator. In yet another preferred embodiment of this aspect of the invention, the macromolecular indicator is associated with the support material in a way that minimizes any hydrophobic influence that a hydrophobic support material will exert on the diffusion distance of the analyte. In yet another preferred embodiment, the macromolecular indicator molecule is, after immobilization, oriented outward into the aqueous surrounding medium. The above embodiments will ensure that the support-indicator construct is well adapted for detecting an analyte in an aqueous environment.

In optical sensing devices, it is generally desirable to have a clear optical path and to be able to expose the sensor to a wide array of wavelengths. Accordingly, one embodiment of the present invention includes a method of immobilizing an indicator molecule on a sensor without introducing optical impurities. In another embodiment of the present invention, the immobilized indicator molecule is resistant to degradation by light at any wavelength to which it will be exposed.

In connection with high throughput manufacturing of immobilized indicator molecules, it is generally desirable that the manufacturing method may be efficient, can be scaled up, and that the immobilized indicator can withstand manufacturing stresses. Accordingly, in one embodiment of the present invention, the immobilization method is highly efficient with respect to indicator usage (immobilization reaction yield) at scale-up. In another embodiment of the present invention, the immobilization method can be readily scaled up and the support-indicator construct can be manufactured at high throughput rates. In yet another embodiment of the present invention, the support-indicator construct can withstand the sterilization methods and wash cycles it will need to be exposed to during manufacturing operations.

In highly sensitive applications, such as in sensors for in vivo applications, it is generally desirable that the quality of the product be consistent. Accordingly, in one embodiment of the present invention, the immobilization method allows for a high degree of "sameness," ensuring device-to-device consistency in calibration and signal processing.

Especially in long term applications, such as in sensor implants, it may be important that the indicator does not negatively affect its surroundings or is not inactivated by prevailing ambient conditions. Accordingly, in one aspect of the present invention, the immobilized indicator molecule is in intimate and direct association with the solid surface of the sensor encasement/waveguide, thus preventing significant leaching of the indicator into the local environment. In another preferred embodiment, the immobilized indicator molecule is substantially resistant to in vivo degradation. In yet another preferred embodiment of the present invention, the support-indicator molecule constructs have sufficient mechanical integrity to withstand forces anticipated within its intended environment of use.

In one aspect of the present invention, a macromolecular indicator molecule may be attached to a support by interlacing the macromolecular indicator with a polymeric structure on the support forming a graft. A "graft" in the context of the present invention is an IPN (interpenetrating polymer network) which may be formed by at least one macromolecular indicator molecule and at least a portion of a polymer chain located preferably near the surface of a support network. An IPN, in the context of the present invention, is a combination of two or more polymers wherein least one is synthesized and/or crosslinked in the immediate presence of the other without any covalent bonds between them. As described in more detail below, in a preferred embodiment, the IPNs of the present invention can be made by sequential polymerization resulting in sequential IPNs. In another preferred embodiment, the IPNs of the present invention are made by interlacing a partially or fully polymerized macromolecular indicator molecule with the polymeric structure of the support, resulting in what is called, in the context of the present invention, an interpenetrating polymer network ("IPN").

A first step in producing a graft is to produce interlacing areas at the surface of the support. An "interlacing area" according to the present invention may be an area near the surface of a support in which polymer chains of the support have been loosened to allow interlacing with a partially or fully polymerized macromolecular indicator molecule or by sequential interpenetrating polymerization.

Interlacing areas and grafts can be produced in different ways. For example, in one embodiment, polymeric chains on the surface of a support are loosened to form interlacing areas by a monomeric component, preferably a hydrophilic monomeric component, such as HEMA (2-hydroxyethyl methacrylate), of the macromolecular indicator molecule that also acts as solvent for the support material. In one embodiment of this aspect of the invention, a graft is formed by polymerizing the hydrophilic monomeric components of the macromolecular indicator molecule that caused the loosening of the polymer chains on the surface of the support, with the remaining components of what eventually forms the macromolecular indicator molecule. Interlacing results from having the polymerization proceed through the interlacing areas to form a sequential IPN. The polymerization creates a mechanical lock between the support and the polymerized macromolecular indicator molecule. The polymerization of the components of the macromolecular indicator molecule also causes interlocking with the loosened polymer chains. In accordance with one embodiment, the polymer chains may be tightened as described, for example, in connection with FIGS. 4A and 4B. The tightening of the polymer chains may be achieved, for example, by removal of the solvent, drying or other means.

In a preferred embodiment of the present invention, the polymerization reaction comprises a radical initiator such as, for example, VA-044 (WAKO Chemical Co., Japan). In yet another preferred embodiment, one or more crosslinkers, such as, for example, EGDMA (ethylene glycol dimethylacrylate), TMPTMA (trimethylolpropane trimethacrylate) or para-toluene sulfonic acid may be added to the polymerization reaction mix to crosslink the macromolecular indicator molecule within the support. In a preferred embodiment, the crosslinking of the macromolecular indicator molecules forms loops, while the loosened support material forms another loop which is interlocked with the loops of the macromolecular indicator molecule(s).

The crosslinking of the macromolecular indicator molecules within the graft is aimed at achieving higher overall reliability of the attachment of the indicator molecule. In yet another preferred embodiment, the polymerization reaction may be run within a mold such as a DELRIN® mold similar to the one shown in FIGS. 6A-6D.

In another embodiment of the present invention, which is illustrated in FIGS. 3 and 4, a graft is formed by first loosening the support material by a solvent and having a partially or fully polymerized macromolecular indicator molecule interlace with the interlacing areas of monomer mixture on the support material. In one embodiment, a crosslinker is added to a mix of solvent and the macromolecular indicator molecules, which links the macromolecular indicator molecules to each other. While the crosslinking may occur before interlacing, the process will, in certain embodiments, continue after interlacing has occurred, thus providing additional stability.

Figure 3C:
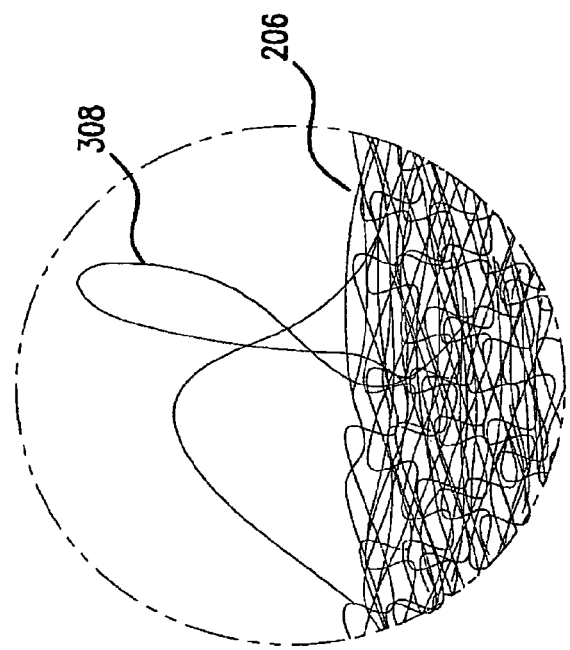
FIGS. 3A to 3C show the creation of interlacing areas at the surface of an immobilization support upon addition of a solvent.
Figure 3A:
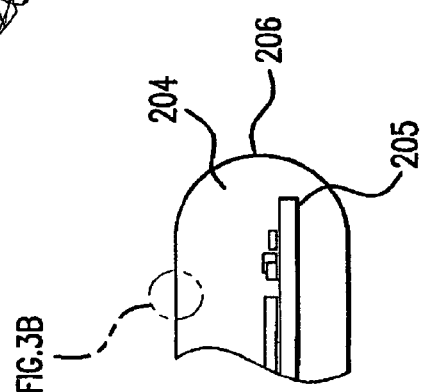
Figure 3B:
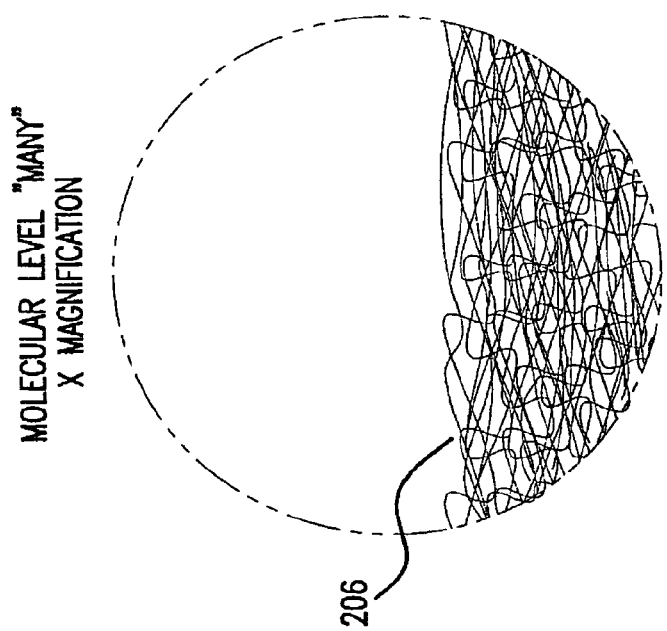

FIG. 3A illustrates a sensor 204 having a polymer encasement for microelectronics 205 as the immobilization support. FIG. 3B is an exploded view of the surface 206 of such the polymer encasement. In this embodiment, the surface comprises a tightly interwoven and intertwined long chained polymer such as PMMA. The arrow pointing from FIG. 3B to FIG. 3C indicates the transition of the surface of the encasement material from a tightly interwoven configuration to a loopy configuration. The loops 308 constitute, in a preferred embodiment, the interlacing areas. This transition is accomplished by treating the surface with a solvent which may be, but is not limited to, ethanol, 2-methoxyethanol, DMF (dimethylformamide), HEMA or mixtures thereof. However, depending on the support material chosen, the person skilled in the art will appreciate that any other substance that can attack the surface of the support to form interlacing areas may be used.

Figure 4B:
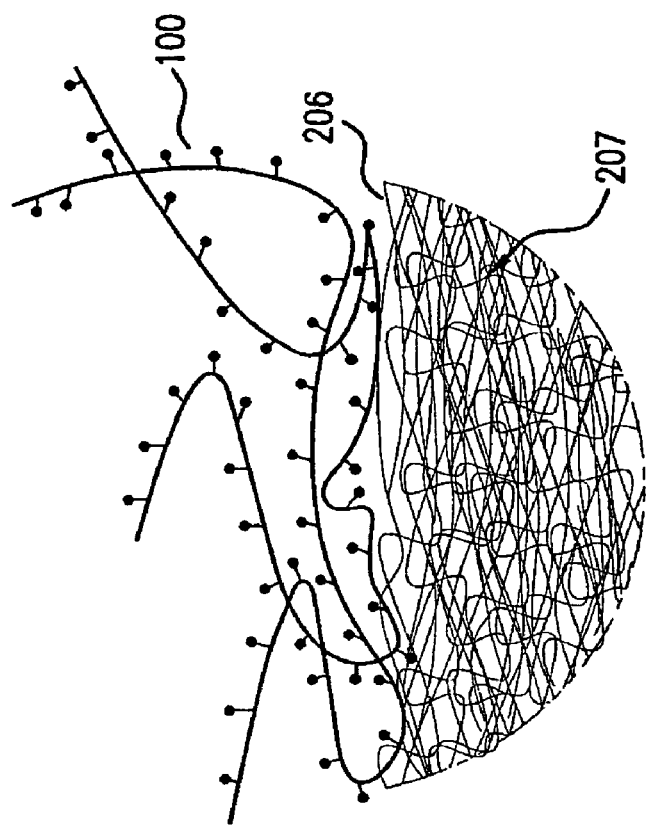
FIGS. 4A and 4B show a mechanism of diffusion of a polymerized macromolecular indicator molecule through an interlacing area and tightening of the interlacing area.
Figure 4A:
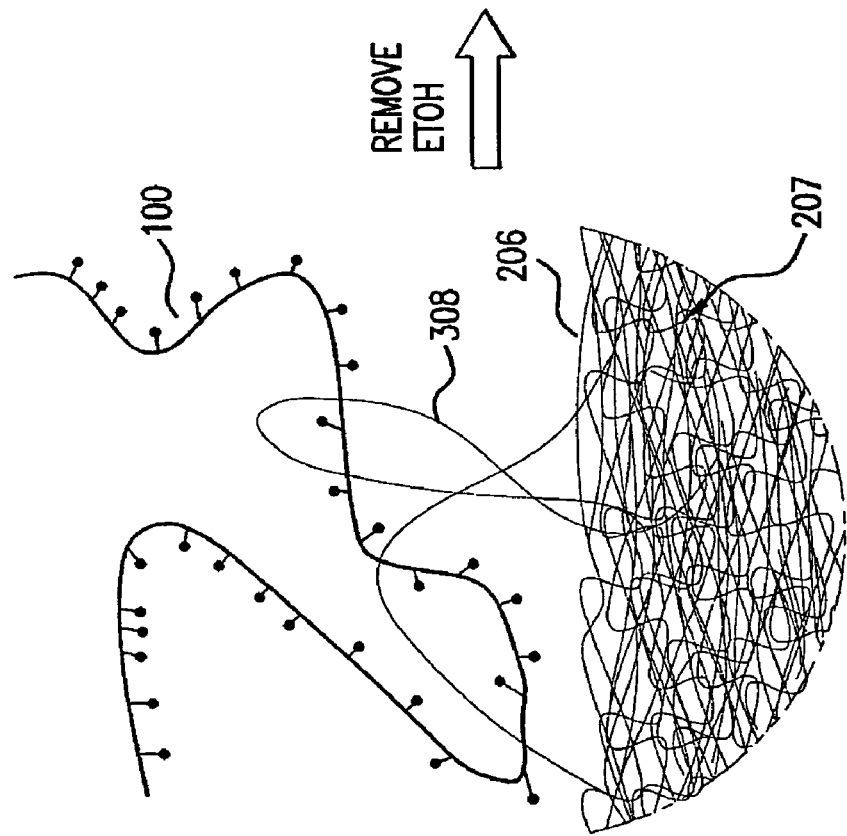

FIG. 4A shows a surface of the support 206 with interlacing areas 308, which may be, for example, created in the manner shown in FIGS. 3A-3C. FIG. 4A also shows a macromolecule, such as a macromolecular indicator molecule 100. The macromolecule is added with the interlacing area forming substance, or after the appropriate interlacing area forming substance has created interlacing areas on a support, to a reaction vessel containing such a support. The macromolecule 100 interlaces with the interlacing areas 308 by, for example, simple diffusion. To accomplish interlacing of the macromolecular indicator molecules substantially evenly over the entire surface of support, e.g., such as a bean shaped sensor device as described in U.S. Pat. No. 6,330,464, the diffusion is allowed to proceed. In a preferred embodiment, the macromolecular indicator and the support are both at least partly soluble in the interlacing area forming substance. In one embodiment, the macromolecular indicator molecule is partially polymerized at the time of interaction with the interlacing areas.

In another embodiment, the macromolecular indicator molecule is fully polymerized at the time of interaction with the interlacing areas. The arrow between FIGS. 4A and 4B indicates the secure immobilization of the macromolecule 100 on the surface of the support as the support material 207 reverts substantially back to its original tight configuration. In this process macromolecule 100 is trapped as shown in FIG. 4B and thus securely immobilized on to the surface of the support material. In a preferred embodiment, this process is accomplished by actively removing the interlacing area creating substance.

In another embodiment of the present invention, the interlacing area creating substance vaporizes over time. In yet another embodiment, the support is dried in the presence of oxygen to slow down the polymerization reaction, which is inhibited by oxygen and thus facilitate diffusion of the macromolecular indicator molecule through the interlacing areas.

In another aspect of the present invention, indicator molecules may be immobilized on a support via ionic bonding. Ionic bonding is based on the electrostatic attraction of ions.

Suitable indicator molecules having ionic charges have been described above. Those indicator molecules may be monomeric or polymeric. Referring to FIG. 5A, a suitable macromolecular indicator molecule 510 is illustrated which has charges 511 distributed over the entire indicator molecule. The molecule is positively charged due to a large number of positively charged moieties 511, for example, amine moieties, which are distributed over the molecule. In contrast, the molecule 520 illustrated in FIG. 5B, contains only a terminal positive charge 522. However, as described above, any indicator molecule carrying positive or negative charges at a suitable pH range can be used in the context of the present invention. In a preferred embodiment, indicator molecules carrying strong positive or negative charges at pHs around neutral are preferred.

Suitable support materials for immobilizing the indicator molecules via ionic bonding in accordance with the present invention have been described above and include, for example, PMMA. However, any support material that is ionic at suitable pH ranges may be used. Such support materials usually are not, but may be, inherently ionic at such pH ranges. Generally, the support materials may be modified to be ionic. For example, a support material may be modified to carry charges that, at a certain pH range, are opposite of the charge(s) of the appropriate indicator molecule that are to be attached to it. In one embodiment, sulfonates, which have been co-polymerized with methyl methacrylate (MMA), are covalently attached to a non-ionic support by methods known from the ion exchange resin art. Ionic groups other than sulfonates may also be used in the context of the present invention. For example, other suitable strong anionic groups such as, but not limited to, methylsulfonate, sulfonic acid, sulfoisobutyl and sulfoethyl can be used in the context of the present invention. Strong cationic groups such as, but not limited to, quaternary ammonium, quaternary amine, trimethylammonium methyl and dimethylyethanolamine can also be used in the context of the present invention. In a preferred embodiment, the groups are ionic at pHs around neutral. While ionic groups can be covalently linked to the support, in a preferred embodiment described above, the ionic groups are provided by coating the support with a copolymer of sulfonate and methyl methacrylate (MMA) or, in certain embodiments, by a glass or glass-like coating. However, other polymers, such as acrylate copolymers, can be used in the context of the present invention.

A process for coating a support in accordance with one embodiment of the present invention is illustrated in FIGS. 6A to 6D. FIG. 6A illustrates a bean shaped sensor 600 and a mold 611 having an inner surface 612 which may be dimensioned to closely match the shape of the sensor 600. As shown in FIG. 6B, when the sensor 600 is inserted into the mold 611, a small gap 613 remains between the surface 606 of the sensor and the inner surface 612 of the mold. FIG. 6C shows how a coating 614 containing ion-exchanger groups, such as a MMA-sulfonate copolymer, is added to the mold to fill this gap. The coating is then cured, for example, by heat, to create a coated sensor device 615, as illustrated in FIG. 6D. FIG. 6D shows the sensing device 615 having a strongly anionic coating 614. As discussed above, the anionic groups of the coating can form ionic bonds with cationic groups, such as amine groups, of an indicator molecule. However, as the person skilled in the art will appreciate, the coating can be applied in a variety of ways including, but not limited to, dipping or spraying.

FIGS. 7A to 7C illustrate the formation of ionic bonds and the resulting immobilization of a positively charged macromolecular indicator molecule on the body of a sensor surface. In particular, FIG. 7A shows the device 615, having a coating 614 having anionic groups 616 equally distributed over its surface. FIG. 7B depicts a macromolecular indicator molecule 510 having positive charges 511 equally distributed over the molecule. The attraction of the negative charges 616 on the sensor support on the one hand, and the positive charges 511 on the macromolecular indicator molecule 510 allow immobilization of the macromolecular indicator molecule on the surface of the support in a simple ion exchange reaction. Thus, the macromolecular indicator molecule can be immobilized on the support as shown in FIG. 7C by bringing it into contact with the support in a solution having a pH value that supports a strongly anionic charge of the support and a strongly cationic charge of the indicator molecule. Since the macromolecular indicator molecule has positive charges distributed over the body of the molecule, these positive charges can form bonds with multiple negative charges on the support 717.

Figure 8C:
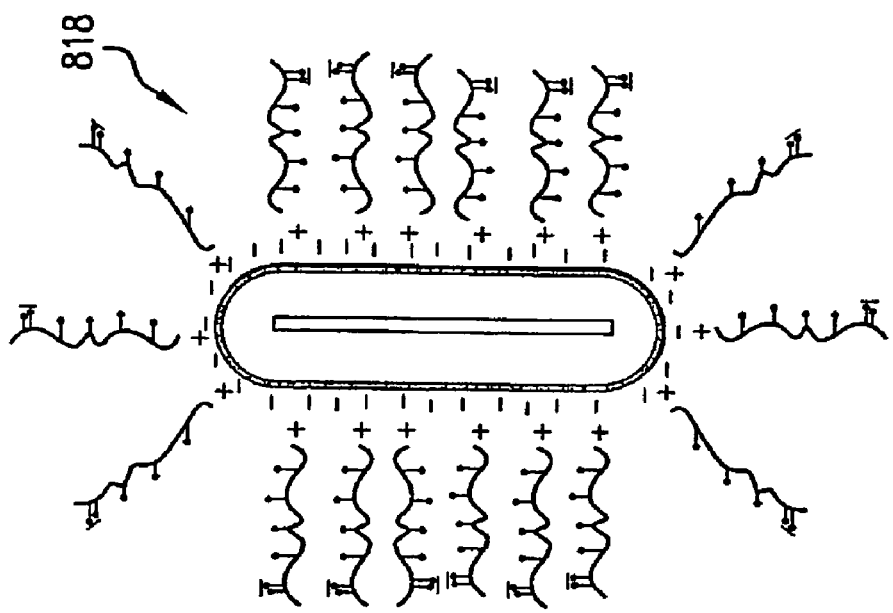
FIGS. 8A to 8C show how a macromolecular indicator molecule carrying a terminal positive charge is attached to a body of a sensor having anionic groups on its surface.
Figure 8B:
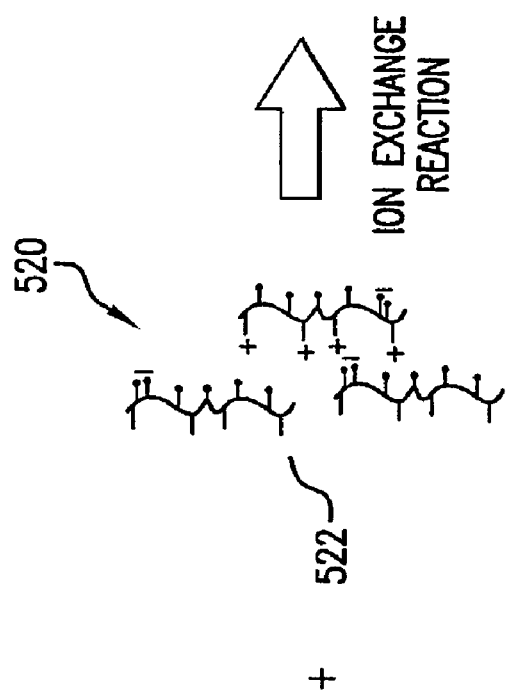
Figure 8A:
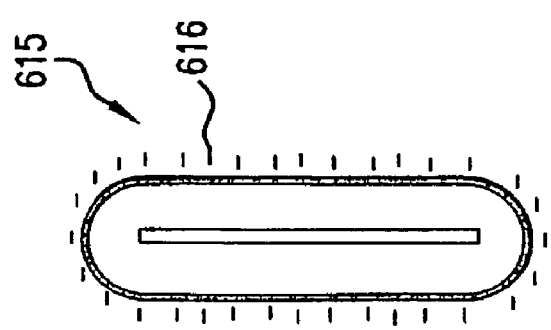

FIGS. 8A to 8C show an immobilization process similar to that shown in FIGS. 7A to 7C. However, the macromolecular indicator molecule 520 carries only a terminal positive charge 522 as opposed to positive charges over the entire body of the molecule as the molecule shown in FIG. 7B. Accordingly, when the macromolecular indicator molecules of FIG. 8B are attached to the anionic substrate 615 via an ion exchange reaction, the indicator molecules are attached to the substrate terminally 818, via an ionic bond between the terminal positive charge in each indicator molecule and an individual negatively charged group on the support.

Example I

An example of a protocol for producing the graft in accordance with one embodiment of the present invention is described below:

Solution A comprising HEMA (95.8%), EGDMA (ethylene glycol dimethacrylate) (0.2%) as a crosslinker and acrylic acid (4%) was provided. A fluorescent monomeric indicator molecule, e.g., bis-carboxylate bis-boronate-anthracene, was added to Solution A at 14 mg/ml (up to about 28 mg/ml) to create "Solution 1." 300 µl of Solution 1 was then added to 700 µl of distilled, deionized water to yield "Solution 2" (white gel). 33.6 µl of a 10% solution (100 mg/ml) of VA-044 (Wako Chemical Co., Japan) (free radical, water soluble initiator molecule) was added to "Solution 2" to create "Solution 3."

In the meanwhile, the immobilization substrate, in this instance a PMMA core, was exposed to ozone for overall 30 minutes in a UVOCS (Model # T0606 ozone chamber) to create hydroxyl groups on its surface to aid in wetting. A thin coating of stopcock grease was applied on the interface of a two part DELRIN® mold. The two mold halves were joined and locked together with three hose clamps (9-22.2 mm) and the bottom hole of the mold was plugged with a rubber septa. The mold was loaded with 200 µl of Solution 3. The internal dimensions of the sensor mold, in this case a 0.203" ID mold, were chosen to ensure that the graft was approximately 100 µm thick. The ozone treated PMMA core was inserted into the mold so that the short bullnose end of the sensor entered the mold first and the sensor optics faced the wall of the mold and was perpendicular to the mold seam while avoiding the formation of air voids. Then the mold was sealed. Heating at approximately 50° C. for approximately 1-24 hours, preferably 3-16 hours, generated a white gel polymer graft. During the heating at 50° C. over an extended period of times, e.g. 3 hrs., the HEMA monomer had time to penetrate the PMMA and interweaving with the PMMA polymer to generate an IPN (interpenetrating polymer network) could proceed. The PMMA core was subsequently removed from the mold and placed in PBS (phosphate buffered saline) storage.

Example II

An example of a protocol for producing the graft in accordance with another embodiment of the present invention is described below:

500 mg of a monomeric indicator molecule, such as bis-carboxylate bis-boronate-anthracene, was added to a 5 g solution comprising HEMA and acrylic acid (90:10; w/w) to create "Solution 1." However, the relative molar ratios of the monomers may be varied to achieve different overall hydrophilicity and control the presence of excimer regions. The relative concentrations of the monomeric indicator molecule and hydrophilic monomer may range, for example, from 750 mg-250 mg indicator to 5 g of Solution A. AIBN (2,2' azo-bis-isobutyronitrile, 98%), a free radical initiator that catalyzes the polymerization of the macromolecular indicator molecule, was added at 1 weight percent to "Solution 1" to create "Solution 2." "Solution 2" was combined with a solution comprising ethanol and 2-methoxyethanol (70:30, w/w) at a weight ratio of 1:10 to create "Solution 3." The solution comprising ethanol and 2-methoxyethanol was added to allow the polymerization reaction to take place and ultimately attack the surface of the PMMA to create interlacing areas. Heating "Solution 3" at approximately 56° C. for approximately 24 hours under nitrogen (to drive off oxygen, which inhibits the pre-polymerization reaction) activated the AIBN initiator causing the polymerization of monomers to create polymers. The resulting "Solution 4," generally contains polymers of differing length as well as un-reacted monomers. "Solution 4" was mixed with the crosslinker para-toluene sulfonic acid (0.333% w/w). The mix was allowed to stand for 2 hours in the dark to yield "Solution 5." The PMMA core was dipped into "Solution 5" and was then allowed to stand in the dark exposed to air for 24 hours. The PMMA core was cured to drive off remaining solvent at 100-110° C. for 3 hours. Excess reaction material, which had not become mechanically fixed to the surface, was washed off in a washing and finishing step.

While various embodiments/variations of the present invention have been described above, it should be understood that they have been presented by way of non-limiting example only. Thus, the breadth and scope of the present invention should not be limited by any of the above-described exemplary embodiments, but should be defined only in accordance with the following claims and their equivalents.

We claim:

1. A method for non-covalently attaching a macromolecular indicator to a support comprising:
   (a) providing a support having an outer surface which comprises at least one polymer, wherein said support is a sensor body or an optical waveguide;
   (b) changing the integrity of the polymer to provide loosened polymer chains that form at least one interlacing area on the surface;
   (c) providing at least one macromolecular indicator or monomers thereof;
   (d) causing the macromolecular indicator to interlace with said at least one interlacing area on the surface, or causing the sequential polymerization of said monomers to form polymerization products which interlace with said at least one interlacing area on the surface; and
   (e) causing the loosened polymer chains to tighten to produce surface immobilized indicator molecules.

2. The method of claim 1, wherein said macromolecular indicator molecule in (c) is a partially or fully polymerized indicator molecule.

3. The method of claim 1, wherein monomers of said at least one macromolecular indicator molecules are provided in (c) and are sequentially polymerized in (d).

4. The method of claim 1, wherein said support surface is hydrophobic or hydrophilic.

5. The method of claim 4, wherein said support surface is hydrophobic and said macromolecular indicator is hydrophilic.

6. The method of claim 1, wherein the integrity of said polymer is changed by the addition of a solvent.

7. The method of claim 6, wherein the loosened polymer chains are tightened by the substantial removal of said solvent.

8. The method of claim 7, wherein the solvent is ethanol, 2-methoxyethanol, dimethylformamide, hydroxyethyl methacrylate or mixtures thereof.

9. The method of claim 7, wherein the solvent is a hydrophilic monomer of a hydrophilic macromolecular indicator.

10. The method of claim 9, wherein the polymerization of said hydrophilic monomer with further monomers of said macromolecular indicator molecule tightens the loosened polymer chains.

11. The method of claim 9, wherein said hydrophilic monomer is 2-hydroxyethyl methacrylate or methacrylamidopropyltrimethylammonium chloride.

12. The method of claim 10, wherein said further monomer of the macromolecular indicator molecule comprises bis-carboxylate bis-boronate-anthracene.

13. The method of claim 1, wherein said macromolecular indicator has at least one reference region.

14. The method of claim 13, wherein said reference region is an excimer region.

15. The method of claim 14, wherein the excimer region is an excimer region resulting from the tertiary structure of the native macromolecular indicator.

16. The method of claim 13, wherein said reference region comprises at least one reference molecule.

17. The method of claim 1, wherein said macromolecular indicator is crosslinked by one or more crosslinkers.

18. The method of claim 17, wherein the one or more crosslinkers are ethylene glycol dimethylacrylate, trimethylolpropane trimethacrylate, para-toluene sulfonic acid or mixtures thereof.

19. The method of claim 17, wherein said at least one macromolecular indicator is crosslinked to another macromolecular indicator molecule after said at least one macromolecular indicator molecule interlaced with at least one interlacing area.

20. The method of claim 17, wherein said at least one macromolecular indicator molecule is crosslinked during sequential polymerization of the monomers of said at least one macromolecular indicator molecule.

21. A method for non-covalently attaching a macromolecular indicator to a support comprising:
(a) providing a support having an outer a surface which comprises at least one polymer, wherein said support is a sensor body or an optical waveguide;
(b) changing the integrity of the polymer to provide loosened polymer chains that form at least one interlacing area on the surface;
(c) providing at least one macromolecular indicator or monomers thereof; and
(d) causing the macromolecular indicator to interlace with said at least one interlacing area on the outer surface, or causing the sequential polymerization of said monomers to form polymerization products which interlace with said at least one interlacing area on the surface.

22. The method of claim 21, wherein said method further comprises the step of (e) causing the loosened polymer chains to tighten to produce surface immobilized indicator molecules.

23. The method of claim 21, wherein said macromolecular indicator molecule in (c) is a partially or fully polymerized indicator molecule.

24. The method of claim 21, wherein monomers of said at least one macromolecular indicator molecules are provided in (c) and are sequentially polymerized in (d).

25. The method of claim 21, wherein said support surface is hydrophobic or hydrophilic.

26. The method of claim 1, wherein the polymer in step (a) is an optically transmissive polymer.

27. The method of claim 26, wherein the polymer is selected from the group consisting of polymethylmethacrylate (PMMA), polystyrene and polycarbonate.

28. The method of claim 27, wherein the polymer is polymethylmethacrylate (PMMA).

29. The method of claim 21, wherein the polymer in step (a) is an optically transmissive polymer.

30. The method of claim 29, wherein the polymer is selected from the group consisting of polymethylmethacrylate (PMMA), polystyrene and polycarbonate.

31. The method of claim 30, wherein the polymer is polymethylmethacrylate (PMMA).

* * * * *